United States Patent [19]

Saeed

[11] 4,070,242

[45] Jan. 24, 1978

[54] METHOD FOR THE PREPARATION OF PROSTAGLANDIN SYNTHETASE

[75] Inventor: Sheikh Arshad Saeed, South Harrow, England

[73] Assignee: Miles Laboratories, Inc., Elkhart, Ind.

[21] Appl. No.: 780,258

[22] Filed: Mar. 23, 1977

[51] Int. Cl.² ............................................. C07G 7/026
[52] U.S. Cl. .................................................. 195/66 R
[58] Field of Search ............................... 195/66 R, 30

[56] References Cited

PUBLICATIONS

Takeguchi et al. in Biochemistry, vol. 10, pp. 2372–2376 (1971).

Flower et al. in Prostaglandins, vol. 4, No. 3, pp. 325–341 (1973).

Yoshimoto et al. in Journal of Biochemistry, vol. 68, pp. 487–499 (1970).

*Primary Examiner*—Lionel M. Shapiro
*Attorney, Agent, or Firm*—James D. McNeil

[57] ABSTRACT

A method for the preparation of purified prostaglandin synthetase from bovine seminal vesicles is disclosed. The method includes the steps of homogenizing bovine seminal vesicles with a liquid medium to form an homogenate and centrifuging the homogenate at a speed such that the centrifugal force does not exceed 1,000g. The supernatant obtained, containing prostaglandin synthetase, is separated from the solids.

7 Claims, No Drawings

METHOD FOR THE PREPARATION OF PROSTAGLANDIN SYNTHETASE

BACKGROUND OF THE INVENTION

Prostaglandin synthetase can be defined as a enzyme complex which catalyzes the oxidative cyclization of unsaturated C-20 fatty acids, e.g., arachidonic acid, into prostaglandins in the presence of a suitable coenzyme.

In 1937, the name "prostaglandin" was coined to describe the pharmacologically active components of seminal fluid. In 1964, the enzymatic conversion of C-20 fatty acids into prostaglandins (hereinafter PGs) was demonstrated simultaneously by two groups of workers led by Van Dorp in Holland and Bergstrom in Sweden [See Biochim. Biophys. Acta 90, 204 and 207 (1964)].

The high degree of interest in PG studies has been prompted by the ubiquity, high potency and varied biological activities of the compounds. Their presence in most tissues and cells of animals has led to investigations into a wide range of therapeutic applications, such as the role of PGs in abortion, nasal congestion, stomach ulcers, asthma, hypertension and inflammation.

It is now generally recognized that PGs play a major role in the inflammatory process and in the generation of inflammatory pain. In 1971, aspirin-like drugs were shown to inhibit PG release from human platelets, to inhibit PG release from perfused dog spleen and to inhibit PG synthesis in guinea pig lung. Inhibition of PG release by aspirin, salicylic acid, indomethacin, and other aspirin-like drugs, has now been demonstrated in some 30 different tissue systems.

The PG synthetase enzymes which are responsible for synthesizing PGs appear to be present in every mammalian tissue so far investigated, although the activity in each tissue varies greatly. In mammalian tissues, the only tissues which have been found to possess high activity are sheep and bovine seminal vesicles (BSV). Because of the high activity, the majority of biosynthetic studies involving conversion of fatty acids into PGs have been conducted using sheep and bovine seminal vesicles as the enzyme source.

PRIOR ART

The original work by Van Dorp and Bergstrom involved PG formation using PG synthetase from ram vesicles. Wallach and Kupiecki examined acetone powder preparations of bovine seminal vesicle homogenates for PG synthetase activity, but found the enzyme activity to be low, on the order of 2 to 10 percent. [See Life Sci. 4, 361 and 1811 (1965)].

This procedure involved blending (homogenizing) the bull seminal vesicles with about 20 volumes of acetone at $-30°$ C. Further operations were conducted at this temperature in a deep freeze. The blended material was first filtered with a vacuum of 25 inches Hg, followed by filtration with high vacuum (less than 25 $\mu$ Hg). The particulate phase (filter cake) was then removed and dried and the seminal vesicle acetone powder used as PG synthetase. Such a procedure is inconvenient, since it involves the use of large amounts of acetone, low temperature operations and high vacuum techniques.

Takeguchi et al, state in Biochem. 10, No. 12, 2372 (1971) that Wallach and Kupiecki found low enzyme activity in the bull seminal vesicle acetone powder preparations, and that further investigations using BSV were abandoned in favor of ram seminal vesicles. Since ram seminal vesicles are difficult to obtain in sufficient quantity, the BSV system was reexamined by Takeguchi et al.

Takeguchi et al. described a procedure in which BSVs were homogenized in phosphate buffer and the homogenate centrifuged at 12,000g. The solids were removed and the liquid filtered through cheesecloth and centrifuged at 105,000g for one hour. The microsomal pellet was collected, lyophilized and used as PG synthetase. The supernatant fraction was discarded. While this procedure resulted in the production of PG synthetase of high enzymatic activity, the collection of the microsomal fraction by high speed centrifugation is time-consuming and involves the use of expensive equipment. The authors disclose that BSV homogenates consistently showed low and varied PG synthetase activity, while BSV microsomes consistently exhibited good activity. The authors further disclose the supposition that an inhibitor of PG synthetase activity was present in the supernatant fraction. In support of this, the authors present data which is stated to demonstrate the inhibition of PG formation by addition of aliquots of the supernatant fraction to an arachidonic acid reaction mixture containing BSV microsomes. Other researchers describe the use of a similar procedure which includes centrifugation at 80,000g for 2½ hours to obtain the microsomal portion of the homogenate. [See Flower et. al., *Prostaglandins*, Vol. 4, (1973) 325–341].

Flower, in *Pharma. Rev.*, Vol. 26, (1974) teaches, with regard to PG synthetase, that microsomal preparations of tissue homogenates are widely used, since . . . "the most important inactivating enzymes are located in the soluble fraction."

Yoshimoto et al. also described the use of the microsomal fraction of BSV. The BSVs were homogenized in phosphate buffer and centrifuged at a high speed (78,000g) for 90 minutes. The microsomal pellet obtained by centrifugation was then used as PG synthetase. [See *J. Biochem.* 68, 487 (1970)].

None of the references discussed above discloses the use of a low-speed centrifugation technique to obtain PG synthetase from the supernatant fraction of bovine seminal vesicles, as disclosed in the instant application.

SUMMARY

The present invention relates to a convenient and economical method of preparing PG synthetase enzyme in high yield. The method involves the steps of homogenizing bovine seminal vesicles with sufficient liquid to form an homogenate and subjecting the homogenate to low speed centrifugation to form a solid and a liquid phase. The centrifugation is conducted at a centrifugal force not exceeding 1,000g. The solids are separated from the liquid phase, and the PG synthetase is present in the supernatant fraction.

Because PG synthetase is involved in the enzymatic conversion of C-20 unsaturated fatty acids into PG compounds, PG synthetase can be tested for enzyme activity by measuring the amount of corresponding PG compound formed from a fatty acid, such as arachidonic acid (5,8,11,14-eicosa-tetraenoic acid). The enzyme activity can be measured by a radio-chromatographic technique employing labelled arachidonic acid as a substrate, based on the loss of one tritium atom that occurs when arachidonic acid is converted to PG. [See *Biochem. Biophys. Res. Commun.* 46, 552 (1972) and *Biochem.* 10, 2372 (1971)]. Alternately, the enzyme activity can be measured by a cascade bioassay technique

[Collier et. al., *Brit. J. Pharmac.* 58, 193-199 (1976)] involving measurement of PG activity against tissue response. The latter technique is described in detail hereinafter.

CASCADE ASSAY SYSTEM

The smooth muscle stimulant effects of the PGs obtained from the enzymatic conversion of arachidonic acid by the PG synthetase obtained by the method of the present invention are determined simultaneously in two different tissues which are known to be contracted by naturally occurring PGs. Segments of rat stomach fundus (stomach strip) and rat colon (colon) are obtained as described in *Brit. J. Pharmacol.* Vol. 5, 173 (1950), Vol. 6, 32 (1953), Vol. 12, 344 (1957), and Vol. 23, 351 (1964). The superfusion technique introduced by Gaddum [*Brit. J. Pharmcol.* 6, 321 (1953)] involves tying one end of the stomach strip preparation to the bottom of a tissue chamber and the other end to a force displacement transducer for continuous tension recording. The tension is adjusted to between 1.5 and 2.0 grams. The tissue preparations are left undisturbed with no solution for at least 15 minutes prior to testing. The tissue chamber has an external water jacket to enable temperature control of the tissues. Water at 40° C is circulated in the water jacket.

The preparations are arranged such that the colon is beneath the stomach strip. The technique consists of dropwise bathing the tissue with a nutrient solution of Kreb's-Ringer bicarbonate bubbled with a mixture of 95 percent $O_2$ and 5 percent $CO_2$ warmed to 37° C. Antagonists are added to the Kreb's solution to eliminate the possibility of smooth muscle responses being due to stimulation of cholinergic, adrenergic, serotonin or histamine receptors. The fluid is circulated by means of a roller pump and is allowed to drip over the tissues at a flow rate of from about 5 to 10 ml/minute.

A dose of standard $PGE_2$ (or $PGF_{2\alpha}$) is put over the tissues by means of the roller pump and the tissue response measured by recording the tissue contraction. A volume of the test solution is then given to the tissue. If the response to the test solution is less than the response to the standard solution, a lower volume of standard is added, to give a lower response than the test response. By this method, the test is always bracketed between two standards, one with a higher response and one with a lower response. To calculate the test value, a logarithmic graph is plotted of the standard value in ng of $PGE_2$ (or $PGF_{2\alpha}$)/ml solution, against the tension response (in mm). The test value obtained is expressed in ng. $PGE_2$ (or $PGF_{2\alpha}$) per volume of test solution injected. Alternately, the protein content of the solution can be determined by known techniques such as the biuret reaction or Kjeldahl method, and the test value expressed in ng. $PGE_2$ (or $PGF_{2\alpha}$) per mg of protein of the test solution. In the dose range used (5-20 ng), $PGE_2$ contracted the fundus tissue but gave only a small contraction on the colon tissue, whereas $PGF_{2\alpha}$ mainly contracted the colon tissue but gave only a small contraction of the fundus tissue.

This technique allows a greater biological sensitivity for biological assays in comparison with tests which involve tissue immersion, since the test solutions are not highly diluted. An additional advantage is that a compound can be tested simultaneously in several tissues by vertical tissue arrangement.

The following solutions were prepared for use in the cascade assay technique.

A. Kreb's-Ringer Solution
The following compounds were added to 5 liters of distilled water:

| | |
|---|---|
| NaCl | 34.5 gm |
| KCl | 1.75 gm |
| $CaCl_2$ | 1.9 gm |
| $KH_2PO_4$ | 0.8 gm |
| $MgSO_4$ | 1.45 gm |
| $NaHCO_3$ | 10.5 gm |
| Glucose | 5.0 gm |

B. Combined Antagonists Solution
The following compounds were made up to 40 ml saline, 0.9 percent (w/v), solution:

| | |
|---|---|
| Hyoscine | 5 mg |
| Mepyramine | 5 mg |
| Phenoxybenzamine | 5 mg |
| Propanolol | 150 mg |
| Methysergide | 10 mg |

C. Standard Solutions
(1) $PGE_2$
Dissolve 1 mg $PGE_2$ in 1 ml of ethanol (96 percent v/v) = 1 mg/ml
Dilute for working standard 10 μg/ml, 100 ng/ml in 0.9 percent (w/v) saline.
(2) $PGF_{2\alpha}$
Repeat $PGE_2$ procedure.

The test solution was prepared by mixing together in a standard assay tube a solution of 50 mM phosphate buffer, 0.25 mM EDTA $Na_2$, 163 μM reduced glutathione (GSH), 91 μM hydroquinone and 500 μl of 15 mg/ml BSV powder solution dissolved in a phosphate buffer, at a pH of 7.4, ionic strength of 50 mM.

Enzymatic reaction was initiated by the addition of 61 μM sodium arachidonate. The assay tube was aerated at 37° C with gentle shaking. After 15 minutes had elapsed, the reaction was stopped by adding 2.0 ml of 0.2 M citric acid. The mixture was then extracted with a 16 ml portion of ethylacetate. After centrifugation for 5 minutes at 600g, 10 ml of the ethylacetate layer was removed and evaporated to dryness in vacuo.

The residue obtained was dissolved in a 400 μl portion of ethanol (96 percent v/v). A 100 μl aliquot of this solution was diluted 50-fold with Kreb's-Ringer solution for cascade assay tests. All experiments included blank controls in which arachidonic acid and the other reagants were incubated with PG synthetase which had been boiled for 3 minutes to inactivate PG synthetase, and extracted as above.

If it is desired to separate the $PGE_2$ from $PGF_{2\alpha}$ for individual quantification, the following procedure can be used.

A 100 μl aliquot of the ethanol solution attained above was chromatographed using the AI solvent system [Green, K. and Samuelson, B., *J. Lipid. Res.*, Vol. 5, 117-120 (1964)] on thin layer silica plates with markers of standard grade $PGE_2$ and $PGF_{2\alpha}$. Following chromatography, the strips corresponding to the marker spots were cut and sprayed with 10 percent phosophomolybdic acid in ethanol and kept at 100° C for 10 minutes. Blue spots appeared in the region of $PGE_2$ and $PGF_{2\alpha}$. The areas corresponding to $PGE_2$ and $PGF_{2\alpha}$ were scraped into test tubes and extracted with ethanol. The ethanol was evaporated to dryness as before, and the residue diluted 50-fold with Kreb's-Ringer solution. It was determined that the PG synthetase of the present invention converted sodium arachidonate into $PGE_2:PGF_{2\alpha}$ in a ratio of 44:1.

The force displacement transducer, tissue chamber and accompanying apparatus were set up as described previously. The roller pump was adjusted to pump the 95 percent $O_2$ –5 percent $CO_2$ Kreb's-Ringer bicarbonate nutrient solution over the tissues at a flow rate of from 5 to 8 ml/minute.

The stomach strip was adjusted to allow the Kreb's-Ringer solution to drip onto the top of the strip, down the strip and off the bottom into the funnel. The colon was set up in the same way. The Kreb's-Ringer solution drips over the stomach strip, over the colon and out to waste.

During testing, the tissues were set up as described and allowed to stabilize with no reagent present for at least 15 minutes. A 20 ng dose of standard $PGE_2$ was then given by injecting the standard into the top funnel and allowing the Kreb's-Ringer solution to wash the standard solution down over the stomach strip and colon.

DESCRIPTION OF THE PREFERRED EMBODIMENT

In order to prepare the PG synthetase according to the present invention, bovine seminal vesicles (BSV) are freed of fat and connective tissues, washed with ice-cold distilled water, cut into small pieces and ground into a coarse mixture. The BSV can be frozen and thawed before use, or can be used as obtained fresh from an abattoir.

About one portion by weight of the ground BSV is mixed with two portions by weight of a liquid aqueous medium. The BSV:liquid medium ratio can range from about 1:1 to about 1:3. The ground BSV-liquid mixture is then homogenized by blending for 2 minutes at top speed, for example, in a Waring Blendor.

The aqueous medium can be distilled or deionized water; the presence of dissolved minerals is undesirable as is the presence of organic contaminants or metal ions. Organic contaminants and metal ions may reduce PG synthetase activity; salts are undesirable because of a tendency to form a precipitate during separation and concentration of the enzyme. In addition to distilled or deionized water, the liquid medium can be phosphate buffer, at a pH of about 7 to 8; 50 mM phosphate buffer can be used.

The homogenate is strained, through cheesecloth or other filter apparatus, to separate fibrous debris. The homogenate is then subjected to low-speed centrifugation to form a solid phase and a liquid supernatant.

The low-speed centrifugation is conducted at from about 500 up to 1,000g, preferably within the range of about 500 to 700g. About 15 to 20 minutes has been found to be sufficient to achieve the desired separation of liquid supernatant and solid fat particles and cell debris. The homogenization and centrifugation are carried out at a temperature in the range of from about 2 to about 6° C. Preferably, the process is carried out at a temperature of up to 4° C.

The supernatant prepared as described above can be used as a source of PG synthetase, or the PG synthetase can be recovered and concentrated by standard isolation techniques known in the art. These techniques include, but are not limited to: (1) fractionation with salts such as ammonium salts, (2) chromatographic techniques using adsorbent columns and elution, (3) ultrafiltration and (4) lyophilization.

The preferred technique for concentrating the PG synthetase from the supernatant is lyophilization. The supernatant is placed into freeze-drying apparatus and saturated with an inert atmosphere, preferably nitrogen. A 95 percent $N_2$, 5 percent $O_2$ inert atmosphere can be used. The supernatant is then rapidly frozen in a dry ice-acetone bath and left on the freeze-drying apparatus until completely dry. For convenience, the PG synthetase powder obtained is pulverized and stored at temperatures of about −20° C to about 4° C.

EXAMPLE

Bovine seminal vesicles (BSV) were freed of fat and connective tissues, washed with ice-cold distilled water, cut into small pieces and ground into a coarse mixture. One portion by weight of ground BSV was mixed with two portions by weight of distilled water and homogenized in a blender for 2 minutes at top speed.

The homogenate obtained was clarified by filtering through a layer of cheesecloth to remove fibrous debris. The resultant homogenate was subjected to a low-speed centrifugation at 600g for 15 minutes. The fat particles and cell debris material were then removed and the supernatant retained.

The PG synthetase present in the supernatant was concentrated by lyophilization. The supernatant was placed into a glass container, saturated with nitrogen, frozen in a dry-ice-acetone bath, and finally left on the freeze-drying apparatus until completely dry. In order to reduce or avoid secondary effects on the material such as loss of activity, the supernatant was frozen as rapidly as possible. The PG synthetase powder obtained was pulverized and stored in bottles at about −20° C until used as described hereinafter.

The PG synthetase obtained by the method of the present invention and bioassayed as described above, had a specific activity of 579 ng $PGE_2$ synthesized/mg BSV protein.

For purposes of comparison, the following experimental procedure was carried out. Ground BSVs were prepared, homogenized and filtered as described in the above Example. The homogenate obtained was subjected to a low-speed centrifugation at 600g for 15 minutes. The supernatant was then further centrifuged for two hours at 100,000g. The supernatant was removed and lyophilized as described in the above Example. The PG synthetase obtained from the supernatant was tested for enzyme activity by measuring the amount of $PGE_2$ activity following the previously-described cascade assay procedure. The PG synthetase obtained had a specific gravity of only 17 ng $PGE_2$ synthesized/mg BSV protein.

The test results indicate that the instant invention provides a method for obtaining a high yield of PG synthetase from the low speed supernatant fraction of BSV homogenate. This high activity of the supernatant fraction obtained by the disclosed method is unexpected, in view of the prior art teachings of the necessity of avoiding the use of the supernatant fraction.

The freeze-dried PG synthetase prepared according to the present invention was subjected to extensive stability tests at various temperatures for a period of up to 2 months.

The tests indicate that the PG synthetase preparation should be stored at low temperatures, about −20° C. Storage at higher temperatures accelerates loss of activity. Tests were also conducted which indicate that the stability of PG synthetase can be greatly improved if 100 μM (0.003 percent w/v) of reduced glutathione is added to the supernatant prior to lyophilization and storage.

What is claimed is:

1. A method for the preparation of prostaglandin synthetase from bovine seminal vesicles which comprises the steps of: homogenizing said vesicles with sufficient liquid medium to form an homogenate, subjecting said homogenate to low-speed centrifugation wherein said centrifugation is sufficient to form a solid phase and a liquid phase, and wherein said centrifugation does not exceed about 1,000g, to obtain a supernatant fraction containing prostaglandin synthetase.

2. A method as claimed in claim 1 wherein the liquid medium consists essentially of water.

3. A method as claimed in claim 1 wherein the ratio of bovine seminal vesicles to liquid medium is from about 1:1 to about 1:3.

4. A method as claimed in claim 1 wherein the liquid medium is phosphate buffer solution.

5. A method as claimed in claim 1 wherein reduced glutathione is added to said supernatant.

6. A method as claimed in claim 1 wherein the prostaglandin synthetase is recovered by lyophilizing said supernatant.

7. A method as claimed in claim 1 wherein, prior to homogenization, said vesicles are washed, freed of fat and connective tissues and ground to a coarse mixture.

* * * * *